(12) United States Patent
Gore et al.

(10) Patent No.: US 7,091,327 B2
(45) Date of Patent: Aug. 15, 2006

(54) PROCESS FOR THE PREPARATION OF AROMATIC AZO-COMPOUNDS

(75) Inventors: Vinayak G. Gore, New Panvel (IN); Manoj M. Ghadge, Navi Mumbai (IN); Vishakha R. Shembekar, Dombivli (IN); R. Venkat Raman, Vashi (IN)

(73) Assignee: Generics [UK] Limited, Hertfordshire (GB)

( * ) Notice: Subject to any disclaimer, the term of this patent is extended or adjusted under 35 U.S.C. 154(b) by 384 days.

(21) Appl. No.: 10/666,819

(22) Filed: Sep. 17, 2003

(65) Prior Publication Data

US 2004/0132982 A1 Jul. 8, 2004

(30) Foreign Application Priority Data

Sep. 17, 2002 (GB) .................................. 0221515.0

(51) Int. Cl.
*C09B 27/00* (2006.01)
*C09B 43/00* (2006.01)
*C07C 245/08* (2006.01)
*A61K 31/655* (2006.01)
*A61P 1/00* (2006.01)

(52) U.S. Cl. .................. 534/599; 534/660; 534/DIG. 5

(58) Field of Classification Search ................ 534/599, 534/660
See application file for complete search history.

(56) References Cited

U.S. PATENT DOCUMENTS 1,157,169 A * 10/1915 Mettler ........................ 534/660
4,528,367 A * 7/1985 Agback et al. ............. 534/599
4,559,330 A * 12/1985 Agback et al. ............. 514/166

FOREIGN PATENT DOCUMENTS

| DE | 276 863 A1 | 3/1990 |
| EP | 0 036 636 | 3/1981 |
| GB | 0221515.0 | 10/1924 |

OTHER PUBLICATIONS

Chen, Chemical Abstracts, 131:219150, 1999.*
Yan et al., Chemical Abstracts, 129:302425, 1998.*

* cited by examiner

*Primary Examiner*—Fiona T. Powers
(74) *Attorney, Agent, or Firm*—Wolf, Greenfield & Sacks, P.C.

(57) ABSTRACT

The present invention relates to a process for the preparation of aromatic azo-compounds, in particular 3,3'-azo-bis(6-hydroxybenzoic acid) (olsalazine) and its salts and derivatives.

10 Claims, 4 Drawing Sheets a: protection
b: $H_2O_2$, AcOH
c: conc. $H_2SO_4$ a: esterification
b: $H_2O_2$, AcOH
c: conc. $H_2SO_4$

PROCESS FOR THE PREPARATION OF AROMATIC AZO-COMPOUNDS

CROSS-REFERENCE TO RELATED APPLICATION

This application claims the benefit of UK patent application no. GB 0221515.0.

TECHNICAL FIELD

The present invention relates to a process for the preparation of aromatic azo-compounds, in particular 3,3'-azo-bis(6-hydroxybenzoic acid) 1 (olsalazine) and its salts and derivatives. The process of the current invention is very efficient and enables the preparation of 3,3'-azo-bis(6-hydroxybenzoic acid) 1 and its salts and derivatives in high yield with low operating costs on a manufacturing scale.

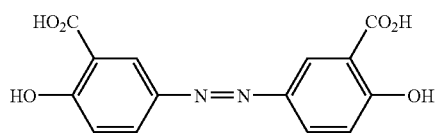

BACKGROUND ART

Certain 3,3'-azo-bis(6-hydroxybenzoic acid) derivatives have useful properties and can be used as pharmaceuticals or dyestuffs. One such compound, the disodium salt of 3,3'-azo-bis(6-hydroxybenzoic acid) 1 [disodium olsalazine 1d] is marketed as a pharmaceutical for the treatment of ulcerative colitis under the trade name Dipentum®.

Processes for the preparation of 3,3'-azo-bis(6-hydroxybenzoic acid) 1 and its salts and derivatives are known and have been disclosed in patents EP 0036636 and DD 276863.

The inventors of the present application have developed a process, particularly useful for industrial scale manufacture, as it is short, simple and high yielding. The process does not use any hazardous or difficult to handle reagents and is an improvement on currently known processes for the industrial scale manufacture of 3,3'-azo-bis(6-hydroxybenzoic acid) 1 and its salts and derivatives.

SUMMARY OF THE INVENTION

A first aspect of the present invention is a process for the preparation of an aromatic azo-compound 4

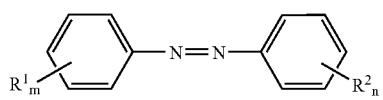

or a salt thereof, comprising the step of treating aromatic amino-compounds 5 and 6

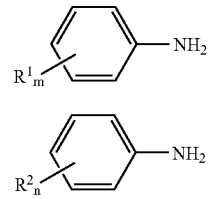

with (i) hydrogen peroxide and acetic acid, followed by (ii) conc. sulphuric acid, to yield aromatic azo-compound 4 or a salt thereof, wherein each m and each n is independently 0, 1, 2, 3, 4 or 5, and
each $R^1$ and each $R^2$ is independently an optionally substituted alkyl, alkenyl, alkynyl, aryl, arylalkyl, arylalkenyl, arylalkynyl, alkylaryl, alkenylaryl or alkynylaryl group which may include one or more heteroatoms N, O or S in its carbon skeleton, —F, —Cl, —Br, —I, —$CF_3$, —$CCl_3$, —$CBr_3$, —$CI_3$, —OH, —SH, —$NH_2$, —CN, —$NO_2$, —COOH, —$R^3$—O—$R^4$, —$R^3$—S—$R^4$, —$R^3$—SO—$R^4$, —$R^3$—$SO_2$—$R^4$, —$R^3$—$SO_2$—$OR^4$, —$R^3$O—$SO_2$—$R^4$, —$R^3$—$SO_2$—$N(R^4)_2$, —$R^3$—$NR^4$—$SO_2$—$R^4$, —$R^3$O—$SO_2$—$OR^4$, —$R^3$O—$SO_2$—$N(R^4)_2$, —$R^3$—$NR^4$—$SO_2$—$OR^4$, —$R^3$—$NR^4$—$SO_2$—$N(R^4)_2$, —$R^3$—$N(R^4)_2$, —$R^3$—$N(R^4)_3^+$, —$R^3$—$P(R^4)_2$, —$R^3$—$Si(R^4)_3$, —$R^3$—CO—$R^4$, —$R^3$—CO—$OR^4$, —$R^3$O—CO—$R^4$, $R^3$—CO—$N(R^4)_2$, —$R^3$—$NR^4$—CO—$R^4$, —$R^3$O—CO—$OR^4$, —$R^3$O—CO—$N(R^4)_2$, —$R^3$—$NR^4$—CO—$OR^4$, —$R^3$—$NR^4$—CO—$N(R^4)_2$, —$R^3$—CS—$R^4$, —$R^3$—CS—$OR^4$, —$R^3$O—CS—$R^4$, —$R^3$—CS—$N(R^4)_2$, —$R^3$—$NR^4$—CS—$R^4$, —$R^3$O—CS—$OR^4$, —$R^3$O—CS—$N(R^4)_2$, —$R^3$—$NR^4$—CS—$OR^4$ or —$R^3$—$NR^4$—CS—$N(R^4)_2$, all optionally protected, wherein each —$R^3$— is independently a chemical bond, a $C_1$–$C_{10}$ alkylene, $C_1$–$C_{10}$ alkenylene or $C_1$–$C_{10}$ alkynylene group, and each —$R^4$ is independently hydrogen, unsubstituted $C_1$–$C_6$ alkyl or unsubstituted $C_6$–$C_{10}$ aryl.

Concentrated sulphuric acid preferably contains at least 95% sulphuric acid, preferably at least 98% sulphuric acid, and more preferably at least 99% sulphuric acid.

Preferably each m and each n is independently 1, 2 or 3.

Preferably each $R^1$ and each $R^2$ is independently an optionally substituted alkyl, alkenyl, alkynyl, aryl, arylalkyl, arylalkenyl, arylalkynyl, alkylaryl, alkenylaryl or alkynylaryl group which does not contain any heteroatoms, —F, —Cl, —Br, —I, —OH, —COOH, —$R^3$—O—$R^4$, —$R^3$—S—$R^4$, —$R^3$—$N(R^4)_2$, —$R^3$—CO—$R^4$, —$R^3$—CO—$OR^4$ or —$R^3$—CO—$N(R^4)_2$, all optionally protected, wherein each —$R^3$— is independently a chemical bond, a $C_1$–$C_{10}$ alkylene, $C_1$–$C_{10}$ alkenylene or $C_1$–$C_{10}$ alkynylene group, and each —$R^4$ is independently hydrogen, unsubstituted $C_1$–$C_6$ alkyl or unsubstituted $C_6$–$C_{10}$ aryl.

More preferably each $R^1$ and each $R^2$ is independently an unsubstituted alkyl, alkenyl, alkynyl, aryl, arylalkyl, arylalkenyl, arylalkynyl, alkylaryl, alkenylaryl or alkynylaryl group which does not contain any heteroatoms, —F, —Cl, —Br, —I, —OH, —COOH, —$OR^4$, —$SR^4$, —$N(R^4)_2$, —COR⁴, —COOR⁴ or —CON(R⁴)₂, all optionally protected, wherein
each —R⁴ is independently hydrogen, unsubstituted $C_1$–$C_6$ alkyl or unsubstituted $C_6$–$C_{10}$ aryl.

For the purposes of the present invention, an "alkyl" group is defined as a monovalent saturated hydrocarbon, which may be straight-chained or branched, or be or include cyclic groups. Examples of alkyl groups are methyl, ethyl, n-propyl, i-propyl, n-butyl, i-butyl, t-butyl and n-pentyl groups. Preferably an alkyl group is straight-chained or branched and does not include any heteroatoms in its carbon skeleton. Preferably an alkyl group is a $C_1$–$C_{12}$ alkyl group, which is defined as an alkyl group containing from 1 to 12 carbon atoms. More preferably an alkyl group is a $C_1$–$C_6$ alkyl group, which is defined as an alkyl group containing from 1 to 6 carbon atoms. An "alkylene" group is similarly defined as a divalent alkyl group.

An "alkenyl" group is defined as a monovalent hydrocarbon, which comprises at least one carbon-carbon double bond, which may be straight-chained or branched, or be or include cyclic groups. Examples of alkenyl groups are vinyl, allyl, but-1-enyl and but-2-enyl groups. Preferably an alkenyl group is straight-chained or branched and does not include any heteroatoms in its carbon skeleton. Preferably an alkenyl group is a $C_2$–$C_{12}$ alkenyl group, which is defined as an alkenyl group containing from 2 to 12 carbon atoms. More preferably an alkenyl group is a $C_2$–$C_6$ alkenyl group, which is defined as an alkenyl group containing from 2 to 6 carbon atoms. An "alkenylene" group is similarly defined as a divalent alkenyl group.

An "alkynyl" group is defined as a monovalent hydrocarbon, which comprises at least one carbon-carbon triple bond, which may be straight-chained or branched, or be or include cyclic groups. Examples of alkynyl groups are ethynyl, propargyl, but-1-ynyl and but-2-ynyl groups. Preferably an alkynyl group is straight-chained or branched and does not include any heteroatoms in its carbon skeleton. Preferably an alkynyl group is a $C_2$–$C_{12}$ alkynyl group, which is defined as an alkynyl group containing from 2 to 12 carbon atoms. More preferably an alkynyl group is a $C_2$–$C_6$ alkynyl group, which is defined as an alkynyl group containing from 2 to 6 carbon atoms. An "alkynylene" group is similarly defined as a divalent alkynyl group.

An "aryl" group is defined as a monovalent aromatic hydrocarbon. Examples of aryl groups are phenyl, naphthyl, anthracenyl and phenanthrenyl groups. Preferably an aryl group does not include any heteroatoms in its carbon skeleton. Preferably an aryl group is a $C_4$–$C_{14}$ aryl group, which is defined as an aryl group containing from 4 to 14 carbon atoms. More preferably an aryl group is a $C_6$–$C_{10}$ aryl group, which is defined as an aryl group containing from 6 to 10 carbon atoms. An "arylene" group is similarly defined as a divalent aryl group.

Where a combination of groups is referred to as one moiety, for example, arylalkyl, arylalkenyl, arylalkynyl, alkylaryl, alkenylaryl or alkynylaryl, the last mentioned group contains the atom by which the moiety is attached to the rest of the molecule. A typical example of an arylalkyl group is benzyl. It should be noted that in the priority application GB 0221515.0, an "alkylaryl" group is defined as encompassing a benzyl group, whereas in the present application a benzyl group is an arylalkyl group.

For the purposes of this invention, an optionally substituted alkyl, alkenyl alkynyl, aryl, arylalkyl, arylalkenyl, arylalkynyl, alkylaryl, alkenylaryl or alkynylaryl group may be substituted with one or more of —F, —Cl, —Br, —I, —CF₃, —CCl₃, —CBr₃, —CI₃, —OH, —SH, —NH₂, —CN, —NO₂, —COOH, —R³—O—R⁴, —R³—S—R⁴, —R³—SO—R⁴, —R³—SO₂—R⁴, —R³—SO₂—OR⁴, —R³O—SO₂—R⁴, —R³—SO₂—N(R⁴)₂, —R³—NR⁴—SO₂—R⁴, —R³O—SO₂—OR⁴, —R³O—SO₂—N(R⁴)₂, —R³—NR⁴—SO₂—OR⁴, —R³—NR⁴—SO₂—N(R⁴)₂, —R³—N(R⁴)₂, —R³—N(R⁴)₃⁺, —R³—P(R⁴)₂, —R³—Si(R⁴)₃, —R³—CO—R⁴, —R³—CO—OR⁴, —R³O—CO—R⁴, —R³—CO—N(R⁴)₂, —R³—NR⁴—CO—R⁴, —R³O—CO—OR⁴, —R³O—CO—N(R⁴)₂, —R³—NR⁴—CO—OR⁴, —R³—NR⁴—CO—N(R⁴)₂, —R³—CS—R⁴, —R³—CS—OR⁴, —R³O—CS—R⁴, —R³—CS—N(R⁴)₂, —R³—NR⁴—CS—R⁴, —R³O—CS—OR⁴, —R³O—CS—N(R⁴)₂, —R³—NR⁴—CS—OR⁴, —R³—NR⁴—CS—N(R⁴)₂ or —R⁴. In this context, —R³— is independently a chemical bond, a $C_1$–$C_{10}$ alkylene, $C_1$–$C_{10}$ alkenylene or $C_1$–$C_{10}$ alkynylene group. —R⁴ is independently hydrogen, unsubstituted $C_1$–$C_6$ alkyl or unsubstituted $C_6$–$C_{10}$ aryl. Optional substituent(s) are not taken into account when calculating the total number of carbon atoms in the parent group substituted with the optional substituent(s).

Any optional substituent may be protected, for example, during the oxidation-dimerization reaction. Suitable protecting groups for protecting optional substituents are known in the art, for example from "Protective Groups in Organic Synthesis" by T. W. Greene and P. G. M. Wuts (Wiley-Interscience, 2$^{nd}$ edition, 1991), which is hereby incorporated by reference in its entirety.

Aromatic amino-compounds 5 and 6 may be the same and together form a symmetric aromatic azo-compound 4. Alternatively, aromatic amino-compounds 5 and 6 may be different and together form an asymmetric aromatic azo-compound 4.

A second aspect of the present invention is a process for the preparation of 3,3'-azo-bis(6-hydroxybenzoic acid) 1

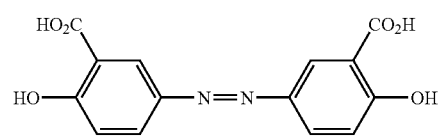

1 or a salt or derivative thereof, comprising the step of treating a 5-amino salicyclic acid derivative 2a

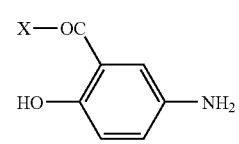

2a or a salt or derivative thereof, with (i) hydrogen peroxide and acetic acid, followed by (ii) conc. sulphuric acid, to yield a 3,3'-azo-bis(6-hydroxybenzoic acid derivative) 1a

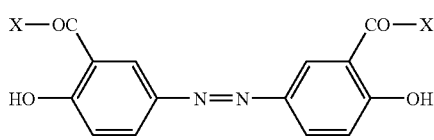

1a or a salt or derivative thereof, wherein

X is OR, SR or $N(R)_2$, when X is OR or SR, R is independently an optionally substituted alkyl, alkenyl, alkynyl, aryl, arylalkyl, arylalkenyl, arylalkynyl, alkylaryl, alkenylaryl or alkynylaryl group which may include one or more heteroatoms N, O or S in its carbon skeleton, hydrogen, —Si(alkyl)$_3$ or —Sn(alkyl)$_3$, and when X is $N(R)_2$, each R is independently an optionally substituted alkyl, alkenyl, alkynyl, aryl, arylalkyl, arylalkenyl, arylalkynyl, alkylaryl, alkenylaryl or alkynylaryl group which may include one or more heteroatoms N, O or S in its carbon skeleton, hydrogen, —SO$_2$-(aryl), —NH$_2$, —NH(alkyl) or —NH(aryl), or both R together form an optionally substituted cycloheteroalkyl, cycloheteroalkenyl or heteroaryl group.

In preferred embodiments, X is a carboxyl protecting group. Suitable carboxyl protecting groups are commonly known in the art, for example from Chapter 5 of "Protective Groups in Organic Synthesis" by T. W. Greene and P. G. M. Wuts (Wiley-Interscience, 2$^{nd}$ edition, 1991), which is hereby incorporated by reference in its entirety.

"Alkyl", "alkenyl", "alkynyl", "aryl", "arylalkyl", "arylalkenyl", "arylalkynyl", "alkylaryl", "alkenylaryl", "alkynylaryl", "alkylene", "alkenylene", "alkynylene" and "arylene" are defined as above with reference to the first aspect of the present invention. A "cycloheteroalkyl", "cycloheteroalkenyl" and "heteroaryl" group is defined accordingly as a cyclic alkyl, alkenyl or aryl group respectively, which comprises at least one heteroatom N, O or S as part of the cyclic system.

For the purposes of this invention, a "salt" of 3,3'-azo-bis(6-hydroxybenzoic acid) 1 is formed between a carboxylic acid functionality of 3,3'-azo-bis(6-hydroxybenzoic acid) 1 and a suitable cation. Suitable cations include, but are not limited to lithium, sodium, potassium, magnesium, calcium and NH$_4^+$. Preferably the salt is a pharmaceutically acceptable salt. Preferably the salt is a lithium, sodium, potassium, magnesium, calcium or NH$_4^+$ salt. More preferably the salt is a sodium salt.

A "derivative" of 3,3'-azo-bis(6-hydroxybenzoic acid) 1 is formed at a carboxylic acid or an alcohol functionality of 3,3'-azo-bis(6-hydroxybenzoic acid) 1. Suitable derivatives include, but are not limited to esters, thiol esters and amides. Preferably the derivative is a pharmaceutically acceptable derivative. Preferably the derivative is an ester, thiol ester or amide.

Most preferably X is OR and R is an optionally substituted alkyl, aryl or arylalkyl group. Preferably X is OR and R is an unsubstituted alkyl group, preferably an unsubstituted C$_1$–C$_6$ alkyl group, more preferably methyl. Alternatively, X is OR and R is an optionally substituted arylalkyl group, preferably benzyl.

The process may further comprise a step of deprotecting the 3,3'-azo-bis(6-hydroxybenzoic acid derivative) 1a to yield 3,3'-azo-bis(6-hydroxybenzoic acid) 1 or a salt or other derivative thereof. Preferably X is OR and a 3,3'-azo-bis(6-hydroxybenzoic acid ester) 1b is deprotected with sodium hydroxide to yield the disodium salt 1d of 3,3'-azo-bis(6-hydroxybenzoic acid). More preferably X is OR, both R are methyl and a dimethyl-3,3'-azo-bis(6-hydroxybenzoate) 1c is deprotected with sodium hydroxide to yield the disodium salt 1d of 3,3'-azo-bis(6-hydroxybenzoic acid).

A third aspect of the present invention is 3,3'-azo-bis(6-hydroxybenzoic acid) 1 or a salt or derivative thereof, obtained by a process of the second aspect of the present invention. A preferred salt of 3,3'-azo-bis(6-hydroxybenzoic acid) 1 is the disodium salt 1d.

A fourth aspect of the present invention is a pharmaceutical composition comprising 3,3'-azo-bis(6-hydroxybenzoic acid) 1 or a salt or derivative thereof, as provided by the third aspect of the present invention, and a pharmaceutically acceptable carrier or diluent.

A fifth aspect of the present invention is a method of treating an inflammatory disease, preferably ulcerative colitis, comprising administering a pharmaceutically effective amount of 3,3'-azo-bis(6-hydroxybenzoic acid) 1 or a salt or derivative thereof, obtained by a process of the second aspect of the present invention, to a subject in need of such treatment.

DETAILED DESCRIPTION OF THE INVENTION

Figure 1:
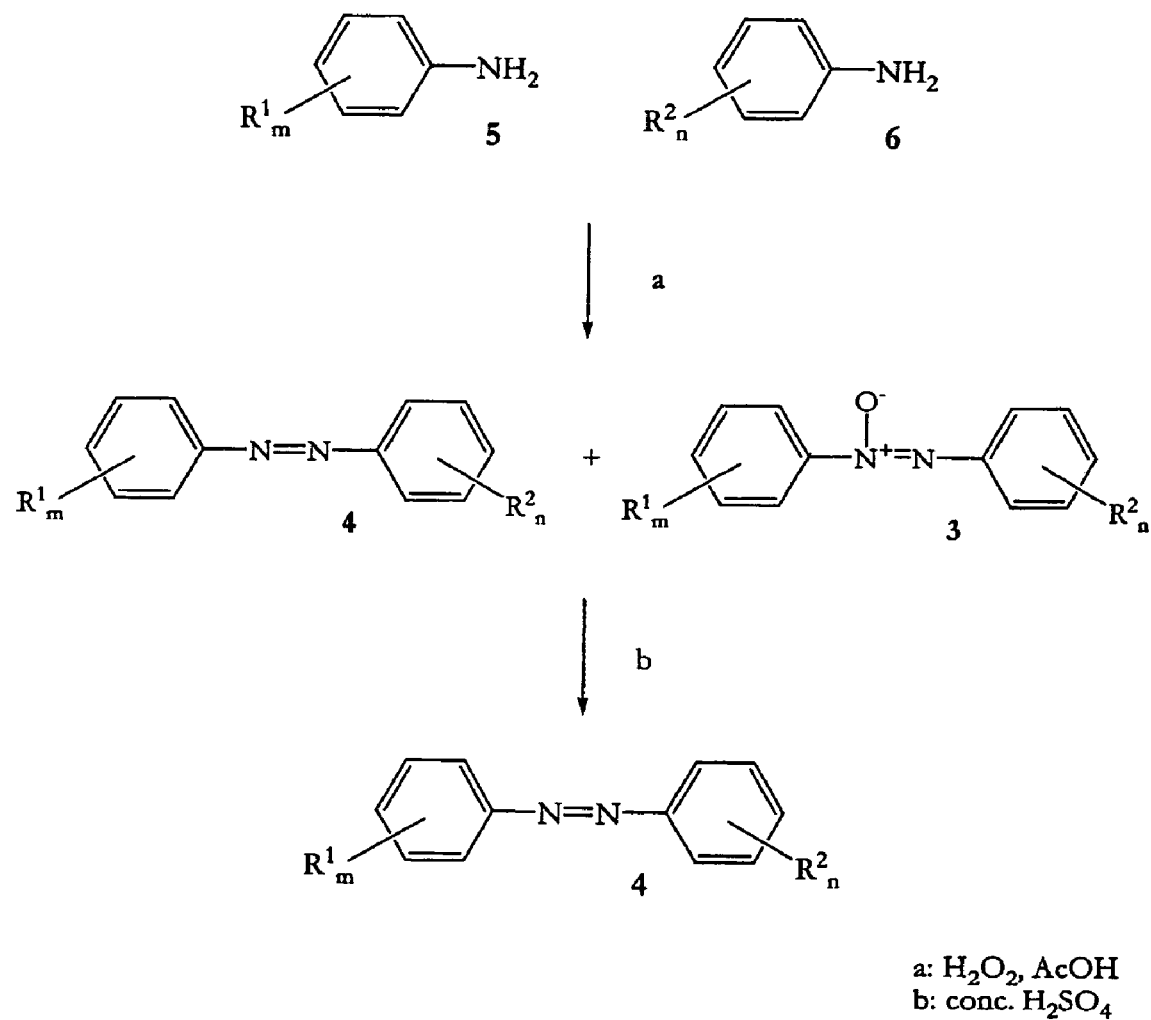
FIG. 1 is a schematic illustration of the general process of the present invention.

A first aspect of the present invention is a process for the preparation of an aromatic azo-compound 4 using an oxidation-dimerization reaction of aromatic amino-compounds 5 and 6 to form the azo-linkage. FIG. 1 outlines a possible reaction mechanism. Two different aromatic amino-compounds 5 and 6 can be used, if an asymmetric aromatic azo-compound is required. The reagents for the oxidation-dimerization reaction are (i) hydrogen peroxide and acetic acid, followed by (ii) concentrated sulphuric acid.

Figure 2:
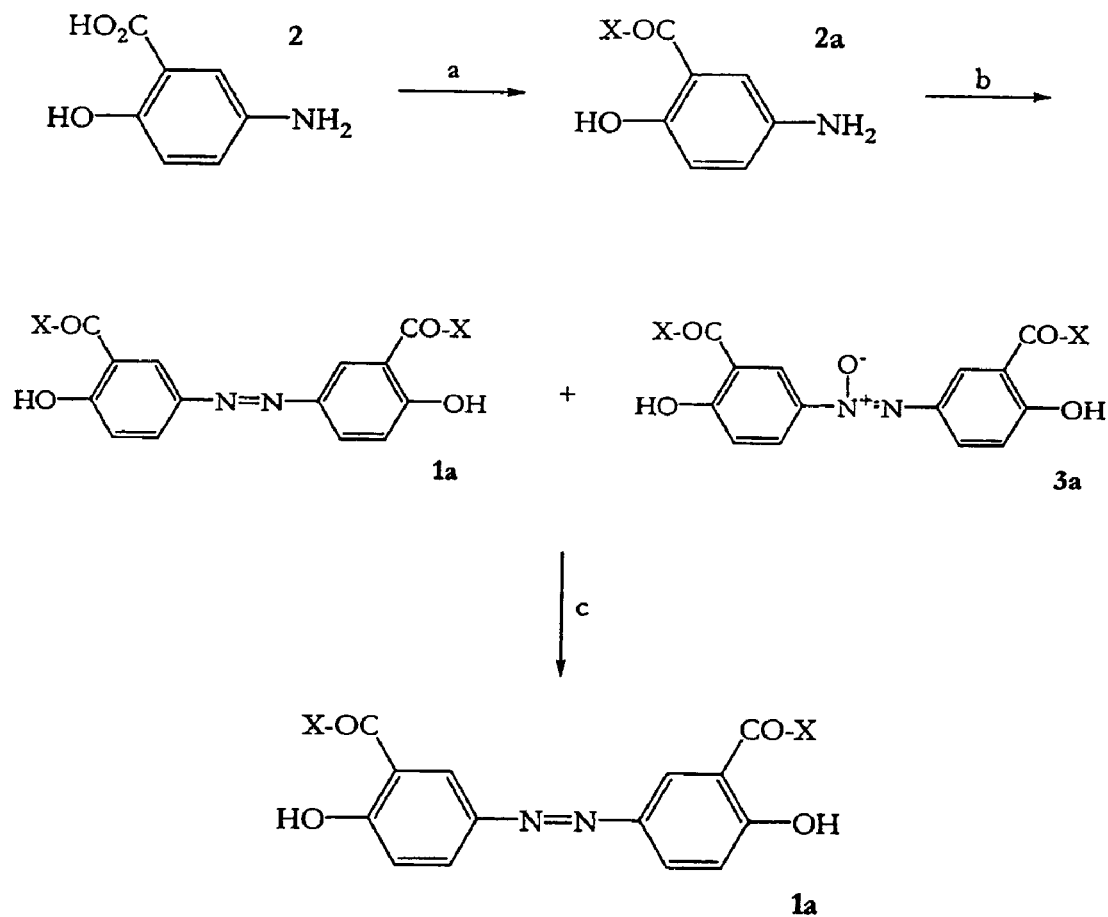
FIG. 2 is a schematic illustration of a preferred process of the present invention for the preparation of 3,3'-azo-bis(6-hydroxybenzoic acid) 1 or a salt or derivative thereof.

A second aspect of the present invention is a process for the preparation of 3,3'-azo-bis(6-hydroxybenzoic acid) 1 (olsalazine) or a salt or derivative thereof, comprising the step of treating a 5-amino salicyclic acid derivative 2a with (i) hydrogen peroxide and acetic acid, followed by (ii) concentrated sulphuric acid, to yield a 3,3'-azo-bis(6-hydroxybenzoic acid derivative) 1a. FIG. 2 outlines a possible reaction mechanism.

As can be seen in FIG. 2, the process involves a key oxidation-dimerization step to form the azo-linkage and to afford the azo-compound 1a. This is a novel approach compared to the prior art for forming the azo-linkage of olsalazine 1 or a salt or derivative thereof. The oxidation-dimerization reaction also produces a by-product 3a, but compound 3a can conveniently be converted to the required azo-product 1a in excellent yield, in the same 'pot', by use of concentrated sulphuric acid.

Figure 3:
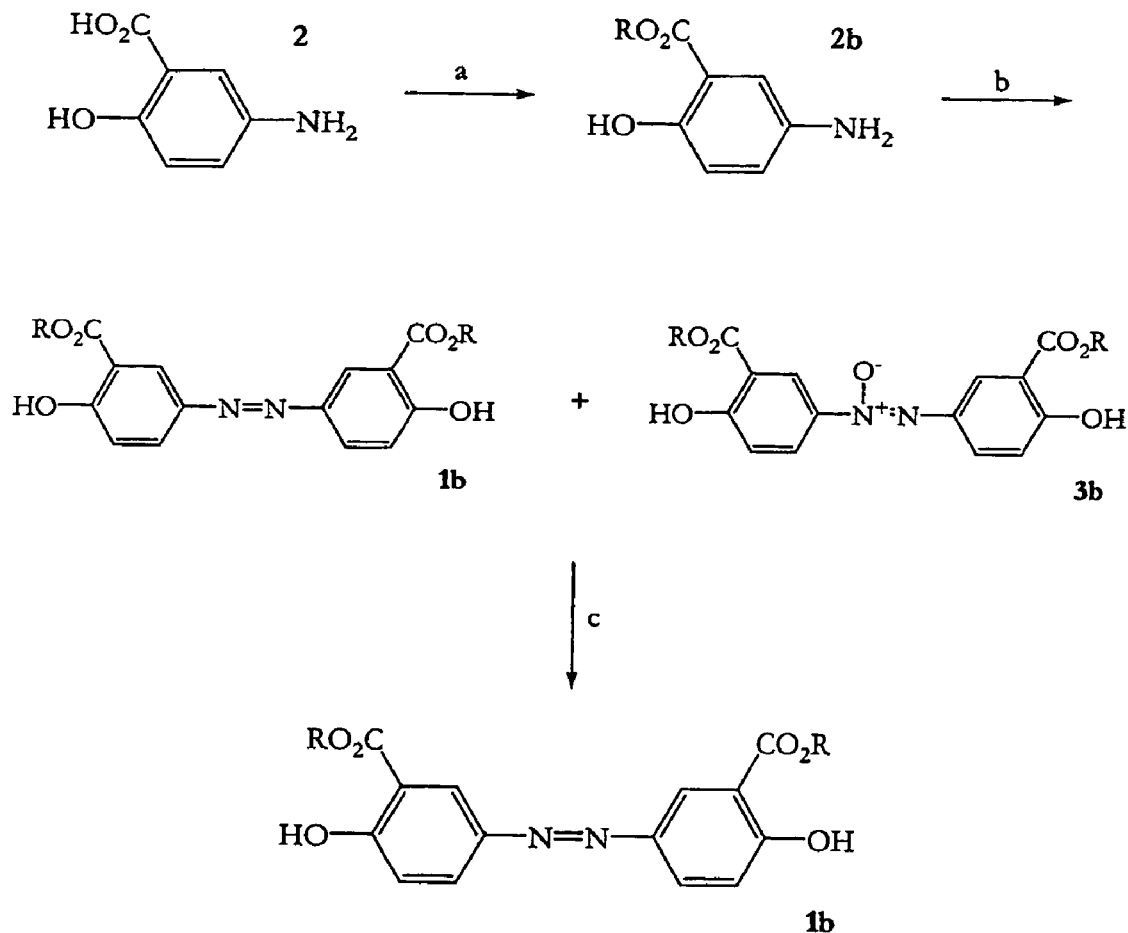
FIG. 3 is a schematic illustration of a preferred process of the present invention for the preparation of 3,3'-azo-bis(6-hydroxybenzoic acid) 1 or a salt or derivative thereof, via the 3,3'-azo-bis(6-hydroxybenzoic acid ester) 1b.

A preferred embodiment of the second aspect of the invention is when 5-amino salicyclic acid derivative 2a is an ester 2b, as illustrated in FIG. 3. Ester 2b is preferably a C$_1$–C$_6$ alkyl ester with R being C$_1$–C$_6$ alkyl. A particularly preferred embodiment is when ester 2b is a methyl ester 2c with R being methyl, as illustrated in FIG. 4.

Figure 4:
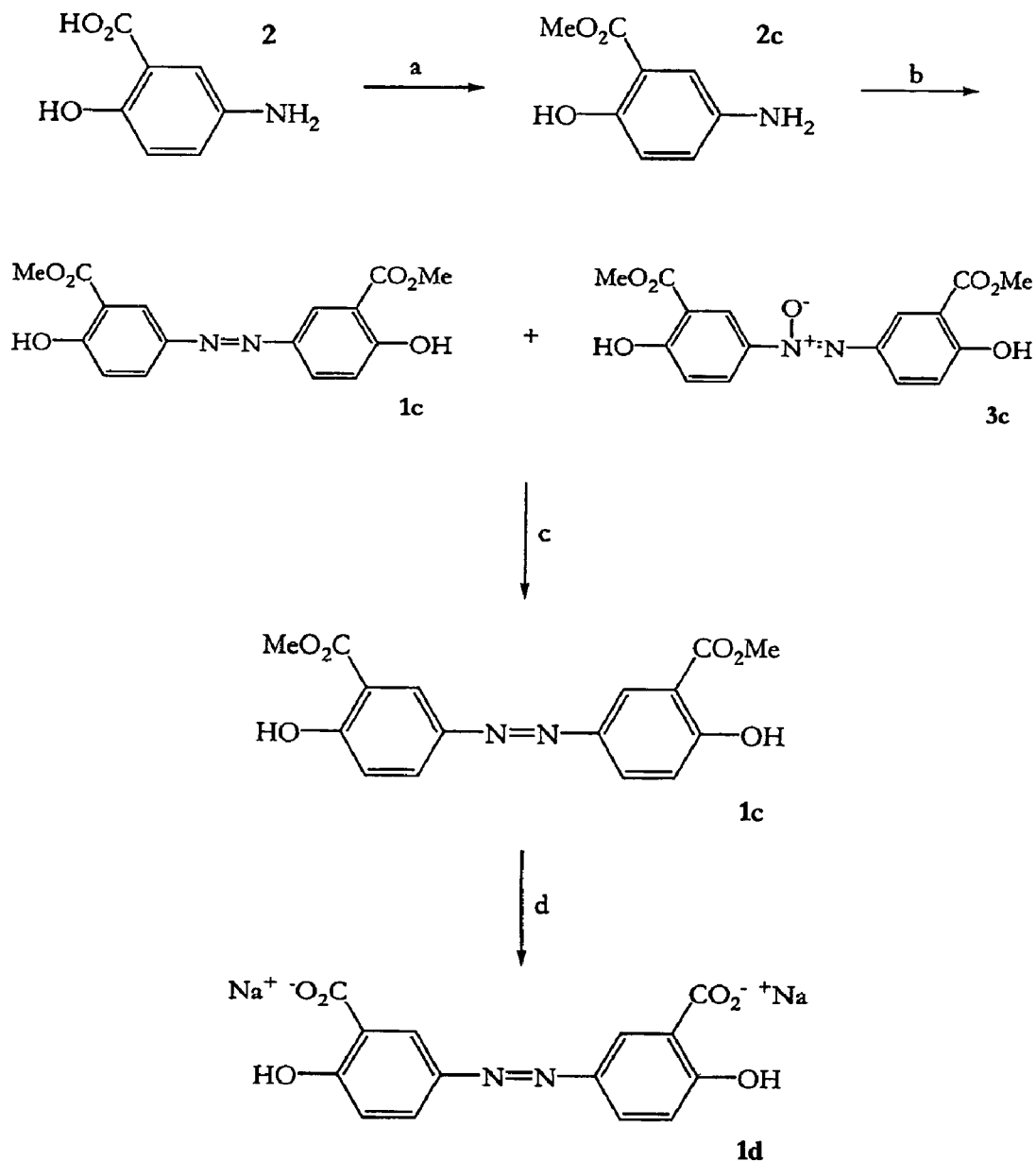
FIG. 4 is a schematic illustration of a preferred process of the present invention for the preparation of 3,3'-azo-bis(6-hydroxybenzoic acid) 1 or a salt or derivative thereof, via the dimethyl-3,3'-azo-bis(6-hydroxybenzoate) 1c.

An example of the process of the second aspect of the invention is the preparation of compound 1d, the disodium salt of 3,3'-azo-bis(6-hydroxybenzoic acid) 1, depicted in FIG. 4. The process illustrated in FIG. 4 is an example of the process of the present invention and detailed procedures for this process are found in the experimental section. Compounds of the present invention are also exemplified in FIG. 4 and in the experimental section.

Further aspects of the current invention are olsalazine 1 and disodium olsalazine 1d, when prepared by a process of the present invention.

The process of the present invention is very efficient and enables the preparation of 3,3'-azo-bis(6-hydroxybenzoic acid) 1 and its salts and derivatives in high yield with low operating costs on an industrial scale. The process is short, simple and high yielding, does not use any hazardous or difficult to handle reagents, and is an improvement on currently known processes for the industrial scale manufacture of 3,3'-azo-bis(6-hydroxybenzoic acid) 1 and its salts and derivatives. Optionally 3,3'-azo-bis(6-hydroxybenzoic acid) 1 and its salts and derivatives may be manufactured in batches of 10 kg or more, or even 30 kg or more.

Experimental Procedure

Methyl 5-amino Salicylate 2c

In a 5 liter four neck flask, fitted with reflux condenser, dropping funnel, thermometer pocket and overhead stirrer, was charged methanol (3500 ml) and 5-amino salicylic acid 2 (500 g, 3.26 mol) with stirring. To the resulting slurry, thionyl chloride (600 ml, 8.16 mol) was added dropwise over a period of two hours by maintaining the temperature of the reaction mass around 35–40° C. After the addition of thionyl chloride was over, the reaction mixture was refluxed for ~15–16 hours. Over the period the reaction mixture became a brown coloured, thin slurry. The progress of the reaction was monitored by thin layer chromatography (tlc). After 5-amino salicylic acid content decreased below 1.0% (based on tlc), the reaction was worked up as follows: methanol (2000 ml) was removed by distillation at atmospheric pressure and remaining methanol was swapped with water (3×1000 ml) under reduced pressure (~200–250 mm of Hg) to get the slurry. This slurry was poured into water (3500 ml) and the pH of the solution was adjusted to ~5.0 with 25% (w/v) NaOH solution (~750 ml) and then to 7.0 to 7.5 with 20% (w/v) $Na_2CO_3$ solution (~300 ml). The precipitated 5-amino methyl salicylate 2c was filtered, and washed with water (2×1000 ml). The cake was dried at 65° C. under reduced pressure (~250 mm of Hg) to constant weight. The yield obtained was 90% (490 g).

M.P.: 93–95° C. [Lit. 93–95° C.; EP 0291159].

$^1$H-NMR (CDCl$_3$): 3.92 ppm (3H, s, Ar—COOCH$_3$); 6.85 ppm (2H, m, Ar—H); 7.16 ppm (1H, d, J=2.73 Hz, Ar—H).

Mass Spec: M$^+$ (167), 135, 107 and 79.

Dimethyl 3,3'-azo-bis(6-hydroxybenzoate) 1c

To glacial acetic acid (500 ml) was charged 5-amino methyl salicylate 2c (250 g, 1.5 mol), while cooling the flask in a water bath (28–30° C.). The resulting slurry was stirred at 28–30° C. for five minutes. To this, aqueous hydrogen peroxide (50% w/v, 300 ml, 4.5 mol) was added over 6 hours. The reaction flask was immersed in water and maintained at 28–30° C. As the addition progressed, the slurry slowly changed into a dark brown-black coloured homogenous liquid. After the hydrogen peroxide addition was over, the reaction mixture was stirred at 28–30° C. The reaction mixture became turbid after ~2–3 hours and a brownish yellow precipitate was observed after 4–5 hours of stirring. After approximately 8 hours of stirring, the reaction mass became a thick brownish yellow slurry. The reaction mixture was stirred for ~22–24 hours, when 5-amino methyl salicylate 2c content was decreased below 1% as seen on tlc. Steps (i) or (ii) could then be followed.

(i) To Isolate a Mixture of 1c and 3c, the Following Procedure Was Followed:

To this reaction slurry was added water (3750 ml) and stirred for 25–30 minutes for complete precipitation of a mixture of dimethyl 3,3'-azo-bis(6-hydroxybenzoate) 1c and dimethyl 3,3'-azoxy-bis(6-hydroxybenzoate) 3c. The precipitated mixture was then filtered and washed with water (2×500 ml). This was then dried at 65° C. under reduced pressure (~250 mm of Hg) to constant weight (moisture content was NMT 1.0%) to get the intermediates mixture in 73% yield (183 g).

$^1$H-NMR (CDCl$_3$): 4.01 ppm [6H, s, 2×Ar—COOCH$_3$ (for azo-diester)]; 4.02 ppm [6H, s, 2×Ar—COOCH$_3$ (for azoxy-diester)]; 7.08 ppm [2H, d, J=8.8 Hz, C-3 and C-3' Ar—H (for azo-diester)]; 7.11 ppm [2H, d, J=8.8 Hz, C-3 and C-3' Ar—H (for azoxy-diester)]; 8.07 ppm (2H, dd, J=8.97 and 2.46 Hz, C-4 and C-4' Ar—H (for azo-diester)]; 8.28 ppm (1H, dd, J=8.88 and 2.49 Hz, C-4 Ar—H (for azoxy-diester)]; 8.42 ppm (1H, dd, J=8.88 and 2.49 Hz, C-4' Ar—H (for azoxy-diester)]; 8.44 ppm (2H, d, J=2.40 Hz, C-6 and C-6' Ar—H (for azo-diester)]; 8.81 ppm (1H, d, J=2.50 Hz, C-6 Ar—H (for azoxy-diester)]; 9.05 ppm (1H, d, J=2.50 Hz, C-6' Ar—H (for azoxy-diester)]; 11.10 ppm [2H, s, C-2 and C-2' Ar—OH (for azo-diester)]; 11.15 ppm [1H, s, C-2 Ar—OH (for azoxy-diester)] and 11.16 ppm [1H, s, C-2' Ar—OH (for azoxy-diester)].

Mass Spec: 346 (M$^+$ for azoxy-diester), 330 (M$^+$ for azo-diester), 314, 298, 282, 254, 179, 165, 151, 133, 119, 105, 91 and 80.

(ii) To Proceed Directly to Pure Product 1c, the Following Procedure Was Followed:

Sulfuric acid (conc., 400 ml) was added slowly to the reaction mixture over 2.5 hours. The resulting red coloured slurry was stirred for 10 minutes and then heated to 85–90° C. and held at this temperature for 4 hours. The progress of the reaction (disappearance of 3c) was monitored by $^1$H-NMR. After 4 hours the signal at 9.05 ppm, which is characteristic of 3c, disappeared. The reaction mass was cooled to 20–25° C. and quenched by carefully adding it into cold water (10–15° C., 1500 ml), maintaining the temperature of the quenched mass below 35° C. The quenched mass was stirred for 30 minutes and then filtered. The filter cake was washed with warm water (45–50° C.) (2×200 ml) and then with methanol (2×50 ml) and suck dried. This was then dried at 80° C. under reduced pressure (~250 mm of Hg) to constant weight. The yield of the tide compound 1c was 85% (83 g).

M.P.: 223–228° C.

$^1$H-NMR (CDCl$_3$): 4.02 ppm (6H, s, C-1 and C-1' Ar—COOCH$_3$); 7.10 ppm (2H, d, 8.94 Hz, C-3 and C-3' Ar—H); 8.07 ppm (2H, dd, J=8.94 and 2.46 Hz, C-4 and C-4' Ar—H); 8.44 ppm (2H, d, J=2.46 Hz, C-6 and C-6' Ar—H); 11.10 ppm (2H, s, C-2 and C-2' Ar—OH, exchanged with D$_2$O).

Mass Spec: 330 (M$^+$), 298, 179, 163, 151, 135, 107, 91 and 79.

3.3'-azo-bis(6-hydroxybenzoic acid) disodium salt 1d

To a solution of sodium hydroxide (48 g, 1.2 mol in 800 ml of water) was charged compound 1c (80 g, 0.24 mol) at 25–30° C. The resulting dark black-red coloured solution was heated to mild reflux (reaction mixture temperature ~85–90° C.) and was held for 90 minutes. This was then treated with activated carbon and refluxed further for 30 minutes. Then the reaction mixture was cooled to 45–50° C. and was filtered through a celite bed (prepared in water). The celite bed was washed with water (4×80 ml) and was mixed with the main filtrate. Further 240 ml of water was added to the combined filtrate and washings and cooled to 25–30° C. with efficient stirring. The pH of this resulting solution was adjusted to 6.0±0.05 with dropwise addition of 20% v/v aqueous acetic acid over 30–45 minutes. The resulting yellow slurry was cooled to 0–5° C. and stirred for 30 minutes to complete the crystallization. Compound 1d thus obtained was filtered and washed with water (2×160 ml) followed by isopropanol wash (2×40 ml). The wet cake obtained (107 g) was dried at 70° C. under reduced pressure (~650 mm of Hg) for 16 hours to constant weight. The title compound 1d was obtained in 65% yield (55 g).

$^1$H-NMR (DMSO-d$^6$): 6.89 ppm (2H, d, J=8.73 Hz, C-3 and C-3' Ar—H); 7.85 ppm; (2H, dd, J=8.73 and 2.20 Hz, C-4 and C-4', Ar—H); 8.24 ppm (2H, d, J=2.20 Hz, C-6 and C-6' Ar—H).

Mass Spec: 302 (M$^+$−2Na), 284, 266, 214, 165, 137, 121, 109, 93 and 81.

It will be understood that the present invention has been described above by way of example only. The examples are not intended to limit the scope of the invention. Various modifications and embodiments can be made without departing from the spirit and scope of the invention, which is defined by the following claims.

The invention claimed is:
1. A process for the preparation of 3,3'-azo-bis(6-hydroxybenzoic acid) 1

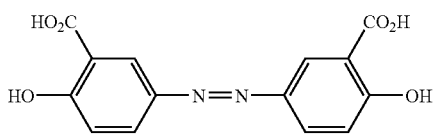

or a salt or derivative thereof, comprising the step of treating a 5-amino salicyclic acid derivative 2a

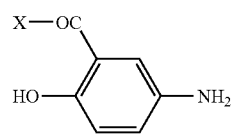

or a salt or derivative thereof, with (i) hydrogen peroxide and acetic acid, followed by (ii) conc. sulphuric acid, to yield a 3,3'-azo-bis(6-hydroxybenzoic acid derivative) 1a

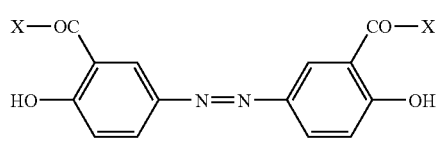

or a salt or derivative thereof, wherein
X is OR, SR or N(R)$_2$,
when X is OR or SR, R is independently an optionally substituted alkyl alkenyl, alkynyl, aryl, arylalkyl, arylalkenyl, arylalkynyl, alkylaryl, alkenylaryl or alkynylaryl group which may include one or more heteroatoms N, O or S in its carbon skeleton, hydrogen, —Si(alkyl)$_3$ or —Sn(alkyl)$_3$, and
when X is N(R)$_2$, each R is independently an optionally substituted alkyl, alkenyl, alkynyl, aryl, arylalkyl, arylalkenyl, arylalkynyl, alkylaryl, alkenylaryl or alkynylaryl group which may include one or more heteroatoms N, O or S in its carbon skeleton, hydrogen, —SO$_2$-(aryl), —NH$_2$, —NH(alkyl) or —NH(aryl), or both R together form an optionally substituted cycloheteroalkyl, cycloheteroalkenyl or heteroaryl group.

2. A process as claimed in claim 1, wherein X is OR and R is an optionally substituted alkyl, aryl or arylalkyl group.

3. A process as claimed in claim 2, wherein X is OR and R is an unsubstituted alkyl group.

4. A process as claimed in claim 3, wherein X is OR and R is an unsubstituted C$_1$–C$_6$ alkyl group.

5. A process as claimed in claim 4, wherein X is OR and R is methyl.

6. A process as claimed in claim 2, wherein X is OR and R is an optionally substituted arylalkyl group.

7. A process as claimed in claim 6, wherein X is OR and R is benzyl.

8. A process as claimed in claim 1, further comprising a step of deprotecting the 3,3'-azo-bis(6-hydroxybenzoic acid derivative) 1a to yield 3,3'-azo-bis(6-hydroxybenzoic acid) 1 or a salt or other derivative thereof.

9. A process as claimed in claim 8, wherein X is OR, and a 3,3'-azo-bis(6-hydroxybenzoic acid ester) 1b

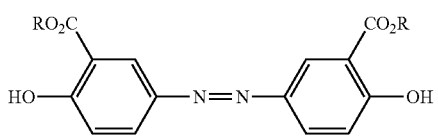

is deprotected with sodium hydroxide to yield the disodium salt 1d of 3,3'-azo-bis(6-hydroxybenzoic acid)

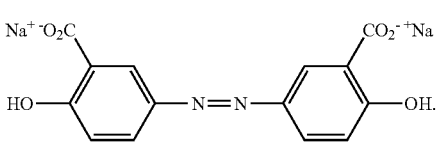

10. A process as claimed in claim 9, wherein X is OR, both R are methyl, and a dimethyl-3,3'-azo-bis(6-hydroxybenzoate) 1c

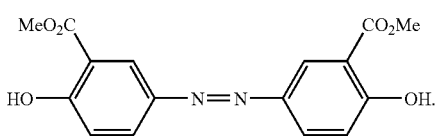

is deprotected with sodium hydroxide to yield the disodium salt 1d of 3,3'-azo-bis(6-hydroxybenzoic acid)

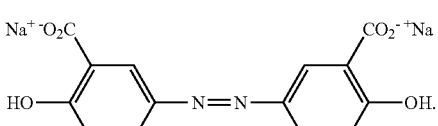

* * * * *